United States Patent
Obayan et al.

(10) Patent No.: US 6,852,541 B2
(45) Date of Patent: Feb. 8, 2005

(54) RAPID ASSAY FOR TESTING OVERALL OXIDATIVE STRESS

(76) Inventors: Adebola Obayan, 14-1128 McKercher Drive, Saskatoon, Saskatchewan (CA), S7H 4Y7; Bernhard H. Juurlink, 251 Whiteswan Dr., Saskatoon, Saskatchewan (CA), S7K 4M6

( * ) Notice: Subject to any disclaimer, the term of this patent is extended or adjusted under 35 U.S.C. 154(b) by 319 days.

(21) Appl. No.: 09/766,522

(22) Filed: Jan. 19, 2001

(65) Prior Publication Data

US 2002/0098591 A1 Jul. 25, 2002

(51) Int. Cl.$^7$ ............................................. G01N 33/00
(52) U.S. Cl. ..................... 436/68; 436/8; 436/16; 436/63; 436/62; 436/84; 436/161; 436/162; 436/164; 436/166; 436/169; 436/174; 436/810; 436/811; 436/815; 422/61; 422/56; 422/68.1; 422/79; 422/82.05
(58) Field of Search ................. 439/8, 16, 63, 439/62, 84, 161, 162, 164, 166, 169, 174, 810, 811, 815; 422/61, 56, 68.1, 79, 82.05

(56) References Cited

U.S. PATENT DOCUMENTS 4,904,605 A * 2/1990 O'Brien et al. ............. 436/169
5,702,955 A * 12/1997 Pugia ......................... 436/135

OTHER PUBLICATIONS

Draper, et al., *Lipids*, 19:836–843 (1984).
Halliwell et al., *Analytical Biochemistry*, 165, 215–219 (1987).
Gutteridge and Halliwell, *Biochem. J.*, 253:932–933 (1988).
Nourooz–Zadeh et al.; *Analytical Biochem.*, 220, p. 403–409 (1994).
Long et al., *Biochem. Biophys. Res. Comm.*, 262:605–609 (1999).
Cadenas et al., *Pharm. & Tox.*, 79, 247–253 (1996).

* cited by examiner

*Primary Examiner*—Lyle A. Alexander
*Assistant Examiner*—Monique T. Cole
(74) *Attorney, Agent, or Firm*—Dilworth & Barrese LLP

(57) ABSTRACT

The invention relates to an assay for testing oxidative stress of a subject by measurement of oxidants in biological fluids such as urine, plasma, bioreactor medium and respiratory aspirants. There is provided a method of determining oxidative stress in a mammalian subject. The method comprises: obtaining a sample of a biological fluid from the subject; mixing the biological fluid with a ferrous reaction reagent; incubating the biological fluid and the reaction reagent; and detecting a colored reaction product.

There is further provided a ferrous reaction reagent suitable for use in assaying oxidative stress, said reaction reagent comprising 2-deoxyglucose, TBA, EDTA, and ferrous sulfate, and being substantially free of ascorbic acid.

35 Claims, 5 Drawing Sheets

(1 of 5 Drawing Sheet(s) Filed in Color)

Standard Curve For Peroxide Equivalent
Assay Using Hydrogen Peroxide

Standard Curve For Peroxide Equivalent Assay Using Hydrogen Peroxide

Hydrogen Peroxide Standards (μmoles/Litre)

Peroxide Equivalents in Urine of Hospital Patients Versus the General Population

* Units x 5 = µmoles/Litre

Urine peroxide Equivalents in Patients and Their Diagnoses

* Units x 5 = μmoles/Litre

RAPID ASSAY FOR TESTING OVERALL OXIDATIVE STRESS

FIELD OF THE INVENTION

The invention relates to an assay for testing oxidative stress of a subject by measurement of oxidants in biological fluids.

BACKGROUND OF THE INVENTION

Oxidative stress has been implicated as a factor in various diseases and injury states. However, the extent to which oxidative stress could be predictive of clinical outcome was unknown, nor was a satisfactory method for rapidly assaying total oxidative stress in a subject available.

Various methods of measuring particular oxidants within biological fluids are known. However, these methods generally rely on the measurement of only a single oxidized compound, or a narrow class of compounds, as indicators of oxidative activity. Thus, they may not be reliable predictors of overall oxidative stress. For example, Draper et al. (*Lipids* 19:836–843, 1984) disclose the use of urinary malondialdehyde as an indicator of lipid peroxidation. These approaches may be limited to the measurement of lipid peroxide breakdown products, and may not adequately reflect oxidation by hydrogen peroxide and organic peroxides.

Attempts have been made to measure oxidative stress through the measurement of hydrogen peroxide in urine (Long et al., BBRC, 262,605–609 (1999)). However, these approaches are limited to the measurement of hydrogen-peroxide derived oxidative species, and may not provide an accurate assessment of overall oxidative stress.

A method of assaying hydrogen peroxide in fluids using 2-deoxyribose was developed by Halliwell, et al. (*Analytical Biochemistry*, 165,215–219 (1987)). Hydroxyl radicals were generated by the reaction of an $Fe^{3+}$ EDTA complex with hydrogen peroxide in the presence of ascorbic acid. These hydroxyl radicals then attacked the deoxyribose to form products which, upon heating with thiobarbituric acid ("TBA") at low pH yield a pink chromogen. The chromogen could then be measured to provide an estimate of the original hydrogen peroxide concentration. However, Halliwell's method is adapted for the measurement of hydroxyl radical, and no consideration was given to the measurement of overall oxidative stress from a range of reactive species. Moreover, the use of ascorbic acid in Halliwell's method renders the reagent mixture relatively unstable, and may render it unsuitable for use in routine clinical testing, and other applications where stability is important. A further disadvantage of Halliwell's method is that the reaction is slow, and of limited accuracy, which may make it unsuitable for use in situations where rapid or precise results are needed.

Thus, it is an object of the present invention to provide a rapid assay for the measurement of overall oxidative stress.

SUMMARY OF THE INVENTION

In an embodiment of the invention there is provided a method of determining oxidative stress in a mammalian subject. The method comprises: obtaining a sample of a biological fluid from the subject; mixing the biological fluid with a ferrous reaction reagent; incubating the biological fluid and the reaction reagent; and detecting a coloured reaction product.

In an embodiment of the invention there is provided a method of identifying a mammalian subject in need of medical treatment. The method comprises: obtaining a sample of a biological fluid and assaying overall oxidant level in the biological fluid.

In an embodiment of the invention there is provided a ferrous reaction reagent suitable for use in assaying oxidative stress, said reaction reagent comprising 2-deoxyglucose, TBA, EDTA, and ferrous sulfate, and being substantially free of ascorbic acid.

In an embodiment of the invention there is provided a kit suitable for use in assaying oxidative stress from a biological fluid. The kit comprises a ferrous reaction reagent and a reference standard.

BRIEF DESCRIPTION OF THE DRAWINGS

The file of this patent contains at least one drawing executed in colour. Copies of this patent with colour drawing(s) will be provided by the Patent and Trademark Office upon request and payment of the necessary fee.

These and other advantages of the invention will become apparent upon reading the following detailed description and upon referring to the drawings in which.

Figure 1:
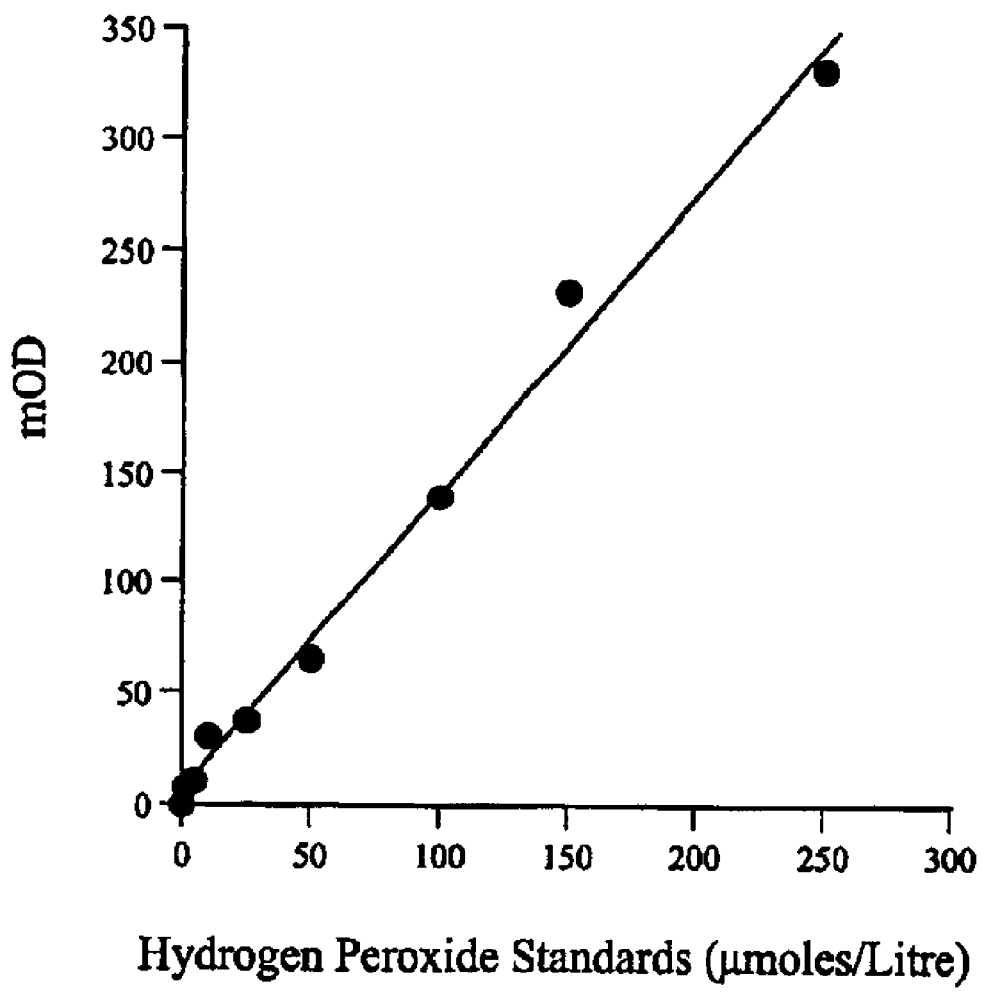
FIG. 1 is a graphical depiction of the results of Example 1.

While the invention will be described in conjunction with illustrated embodiments, it will be understood that it is not intended to limit the invention to such embodiments. On the contrary, it is intended to cover all alternatives, modifications and equivalents as may be included within the spirit and scope of the invention as defined by the appended claims.

DETAIL DESCRIPTION OF THE PREFERRED EMBODIMENTS

The present invention is directed to a rapid assay for the measurement of overall oxidative stress in biological fluids, and to the use of the method in predicting clinical outcome, and identifying subjects warranting further medical examination.

Oxidative stress has been suspected to be linked to the severity of injury or disease in numerous disorders. However, it was not clear whether measurements of oxidative stress could be useful as a predictor of clinical outcome or could be used to guide therapeutic intervention. In particular, previous work had focused on measurements of particular oxidative species, and had failed to provide a satisfactory measure of overall oxidative stress, which could be useful in predicting clinical outcome and guiding therapeutic intervention.

The rapid assay for overall oxidative stress disclosed herein permits measurement of hydrogen peroxide as well as organic peroxides such as lipid peroxides in biological fluids, thereby providing a measure of overall oxidative stress. The method relies on the conversion of peroxides to strong oxidants using the ferrous ($Fe^{2+}$) ion. These strong oxidants react with 2-deoxyglucose to form further reactive products. Additionally, other oxidants such as lipid peroxides, lipid endoperoxides and aldehydes, (including α-oxo-aldehydes, and malondialdehyde aldehydes) are measured by the method of the invention.

The reaction reagent of the present invention overcomes disadvantages of the Halliwell method and is better suited for medical and veterinary applications. In particular, in a preferred embodiment of the invention, the reaction reagent is a ferrous reaction reagent. The use of $Fe^{2+}$ in the ferrous reaction reagent instead of $Fe^{3+}$ renders it unnecessary to use ascorbic acid. Ascorbic acid is relatively unstable, and causes Halliwell's reagent to be unstable. In contrast, the ferrous reaction reagent of the present invention, comprising $Fe^{2+}$, has improved stability.

Surprisingly, it was also found that the use of 2-deoxyglucose and $Fe^{2+}$ instead of 2-deoxyribose and $Fe^{3+}$ as used by Halliwell, permits the faster and more accurate measurement of oxidant levels.

While it is not intended to limit the invention to any particular theory of action, it is believed that many strong oxidants can interact both directly and also indirectly with thiobarbituric acid ("TBA") by the formation of strong oxidants resulting from the reaction of the biological oxidants with 2-deoxyglucose, mediated by ferrous ($Fe^{2+}$) ions.

The present invention permits oxidative stress to be determined using only basic laboratory equipment and without requiring invasive procedures such as intubation. As used herein, the term "minimal method" refers to a method for determining oxidative stress using only basic laboratory equipment (such as a single beam spectrophotometer and graduated cylinders) and capable of being performed without the introduction of instruments or foreign materials into the body of the subject.

The present invention also provides a method for assaying oxidative stress in biological fluids using a solid matrix-associated assay system, such as a "dipstick" method. Such an assay, and a kit for use in such an assay, are suitable for use in homes and veterinary clinic settings, and other locations where sophisticated laboratory equipment is not readily available.

In one embodiment of the invention there is provided a method for determining overall oxidative stress comprising the steps of mixing a biological fluid of interest with a reaction reagent, and incubating the mixture for an appropriate time, following which time the formation of a coloured reaction product is determined. In one embodiment of the invention, light absorption at a wavelength of 532 nM is measured to determine the extent of coloured product formation. Standard curves based on known hydrogen peroxide concentrations can be used to determine the peroxidant equivalent oxidant concentration in biological fluids and such standard curves may be prepared by techniques known in the art.

The ferrous reaction reagent preferably comprises a solution of 2-deoxyglucose, TBA, EDTA, and ferrous sulphate in a suitable solvent, such as distilled water or a suitable buffer such as a physiological potassium phosphate buffer. The ferrous reaction reagent preferably comprises 2-deoxyglucose in a concentration of between about 30 and 400 mM, more preferably between about 50 and 200 mM, even more preferably between about 75 and 150 mM and most preferably of about 100 mM. The ferrous reaction reagent preferably comprises TBA in a concentration of between about 10 and 200 mM, more preferably about 20 and 100 mM, even more preferably between about 40 and 75 mM, most preferably about 50 mM. The ferrous reaction reagent preferably comprises EDTA at a concentration of between about 0.5 and 3 mM, more preferably between about 0.7 and 2 mM, even more preferably between about 1.0 and 1.6 mM, most preferably of about 1.4 mM. The ferrous reaction reagent preferably comprises a concentration of ferrous sulphate of between about 0.5 and 2 mM, more preferably of between 0.75 and 1.5 mM, and most preferably of about 1 mM. In an embodiment of the invention, there is an excess of $Fe^{2+}$, thus there is no need for an electron donor, thereby enhancing the chemical stability of the reaction reagent.

The biological fluid is preferably urine or plasma, although other suitable biological fluids such as bioreactor medium and respiratory aspirates may be employed. A suitable number of parts of the biological fluid is preferably combined with a suitable number of parts of the reaction reagent.

The biological fluid is preferably assayed within 2 hours of its release from the body of the subject, more preferably within 1 hour and most preferably within 15 minutes of its escape. However, it is also effective to store biological fluid at a reduced temperature promptly following its release. For example, urine can be stored at −20° C. for at least 6 months, and plasma can be stored at 4° C. for 10 days, −20° C. for 60 days and −70° C. for one year without substantially impairing the usefulness of the assay. Longer storage times may affect the accuracy of the results obtained, and results from such samples must be examined with reference to oxidant level changes in the fluid during storage, which can be determined in light of the disclosure herein.

When the ferrous reaction reagent comprises 100 mM 2-deoxyglucose, 50 mM TBA, 1.4 mM EDTA and 1 mM $FeSO_4$, the final ratio of ferrous reaction reagent to biological fluid is preferably between about 20:1 and 1:10. Thus, examples of a suitable number of parts of ferrous reaction reagent and a suitable number of parts of biological fluid are one part biological fluid mixed with between 5 and 15 parts of the reaction reagent. More suitably, one part biological fluid is mixed with between 7 and 11 parts of the reaction reagent.

A suitable number of parts of biological fluid to be combined with a particular number of parts of ferrous reaction reagent can be determined by one skilled in the art, in light of the disclosure herein, the dilution of the biological fluid, the optical density of the biological fluid, and the concentrations of 2-deoxyglucose, TBA, EDTA and ferrous sulphate in the reaction reagent.

The mixture of the biological fluid and the ferrous reaction reagent is preferably incubated at between about 20 and 45° C., more preferably between 25 and 40° C., more preferably at about 37° C. The incubation time is preferably between about 0 minutes and 24 hours, more preferably between about 1 minute and 4 hours, even more preferably between about 5 minutes and 30 minutes, and most preferably about 15 minutes.

A solid-support reaction system may be employed by absorbing the reaction reagent on a solid support, such as polyacrylamide gel beads or other suitably inert and porous material, and subsequently exposing the biological fluid or a suitable dilution thereof to the reagent absorbed on the solid support. For example, suitable solid supports include calcium matrices, silica matrices, and porous foam. In one embodiment of the invention, solid support material is immobilized on a non-porous frame, such as a plastic dipstick.

The reaction reagent is preferably absorbed to a solid support and the reagent-support combination sealed in a reduced oxygen environment for use at a later date. In particular, the combination can be sold together with a reference standard providing one or more colour references for oxidant levels as a kit.

In one embodiment, the reaction reagent is absorbed on to a solid support which is dipped in freshly captured urine or held in the urine stream of a patient. Similarly, where the biological fluid is respiratory aspirates, the reagent-support combination is preferably held in the stream of the subject's respiratory release, permitting respiratory aspirants to mix with the reaction reagent. Alternatively, respiratory aspirates are readily collected from intubated subjects, and subjects wearing masks such as face oxygen masks. The patient would then compare the colour change observed to one or more reference standards. In particular, a predominantly light pink colour indicates a normal level of oxidative stress whereas a predominantly dark pink, red, or brown colour, indicates significant oxidative stress warranting medical examination.

Preferably, the subject compares the reaction dipstick to the reference standard between about 0 minutes to 60 days after exposing the dipstick to the biological fluid, more preferably between about 0.5 minutes and 1 day, and even more preferably between about 10 minutes and 24 hours after exposing the dipstick to the biological fluid.

Preferably, the biological fluid is exposed to the reaction reagent immediately following release of the biological fluid from the subject's body. However, storage of samples at reduced temperatures for later analysis is possible, as previously discussed.

EXAMPLE 1

Preparation of Standard Curve

A ferrous reaction reagent comprising 100 mM 2-deoxyglucose, 50 mM thiobarbituric acid, 1.4 mM EDTA, and 1 mM ferrous sulphate in triple distilled water was prepared. Standard concentrations of hydrogen peroxide, ranging from 1 $\mu$M to 250 $\mu$M were prepared in triple distilled water.

500 $\mu$L of each hydrogen peroxide standard were added to 500 $\mu$L each of the reaction reagent, and the mixtures were incubated at 37° C. for 15 minutes. The absorbence of the mixtures at 532 nM was measured after 15 minutes incubation. The results of this experiment are shown in FIG. 1, which shows that absorbence increased in a linear manner with increasing hydrogen peroxide concentration.

EXAMPLE 2

Analysis of Oxidant Levels in Plasma and Urine

Figure 2:
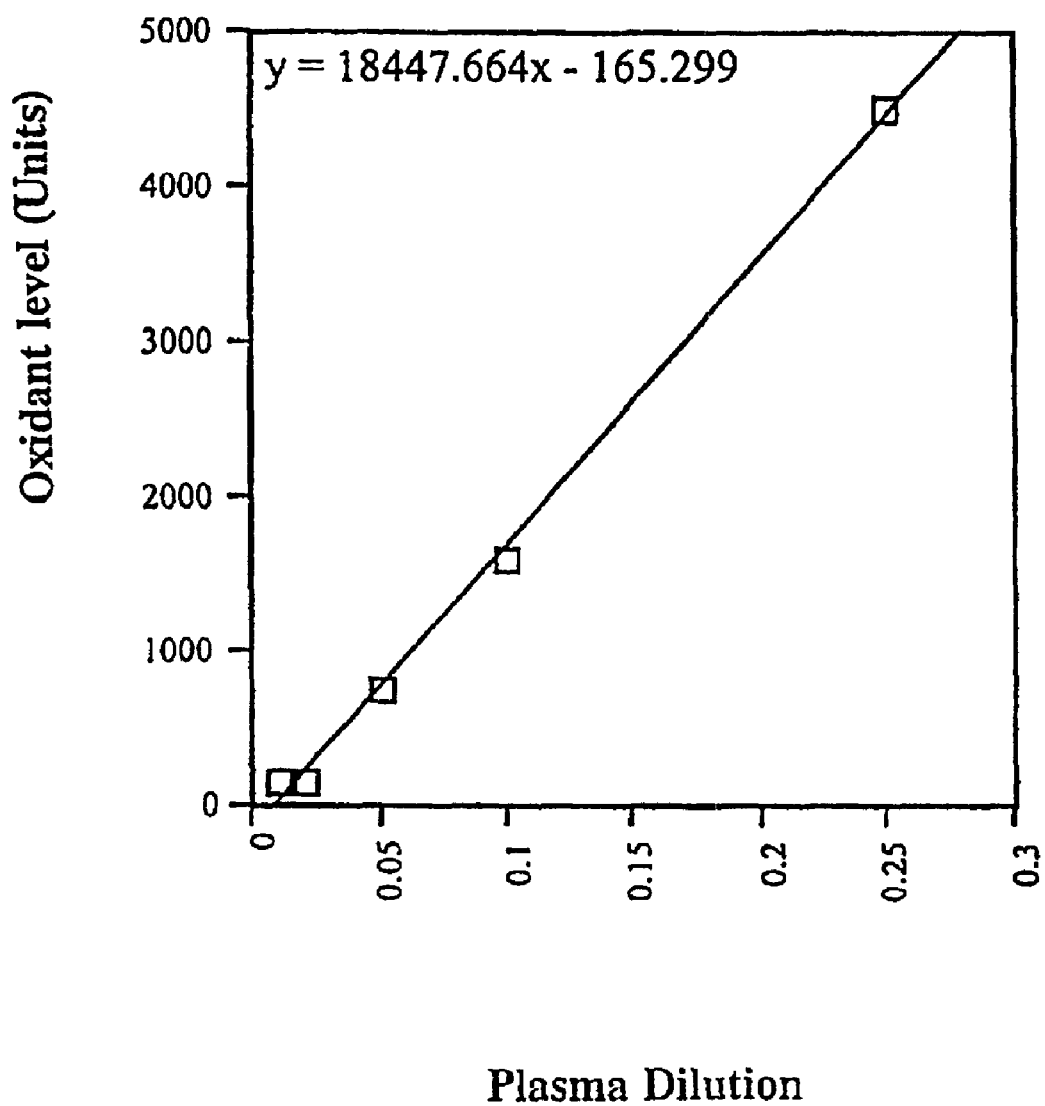
FIG. 2 is a graphical depiction of the results of Example 2.

Plasma was obtained from whole human blood by standard techniques. Plasma was diluted to a fraction of its initial concentration (defined as "1") in 0.01M potassium phosphate buffer (pH7.4). The peroxide-equivalent overall oxidant level was determined, by mixing 100 $\mu$L of each plasma dilution with 900 $\mu$L of the ferrous reaction reagent prepared as in Example 1, incubating the mixtures at 37° C. for 15 minutes, and measuring absorbence at 532 nM after 15 minutes. The results are depicted in FIG. 2 (Numbers on the x-axis refer to the dilution of the plasma. "0" refers to no plasma present, "0.1" indicates a 10-time dilution and "0.25" indicates a 4-time dilution. The y-axis depicts the oxidant "units" present in samples, wherein 1 unit=5 $\mu$M hydrogen peroxide equivalent.) The results indicated that the assay of the present invention is an accurate measure of overall oxidant levels in plasma.

EXAMPLE 3

Use of Assay in Predicting Clinical Outcome

The oxidant concentration in urine of patients admitted to hospital for various conditions was assessed using the method of the present invention, and was compared to the oxidant concentration in urine obtained from members of the general population.

Figure 3A:
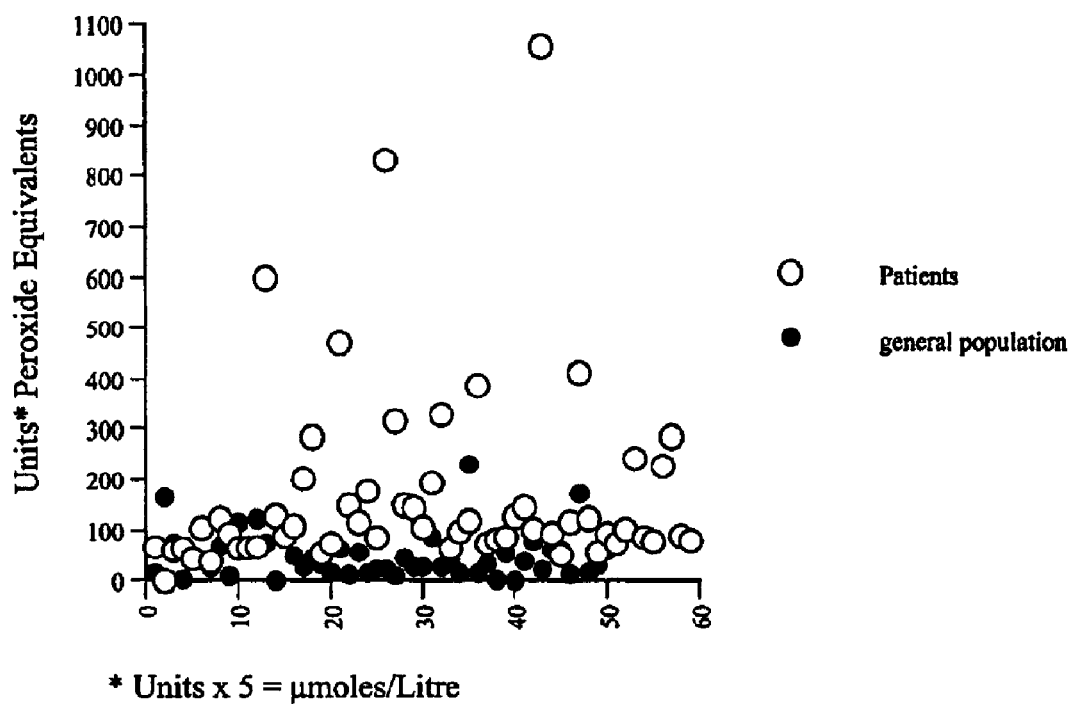
FIGS. 3a and 3b are graphical depictions of the results of Example 3.
Figure 3B:
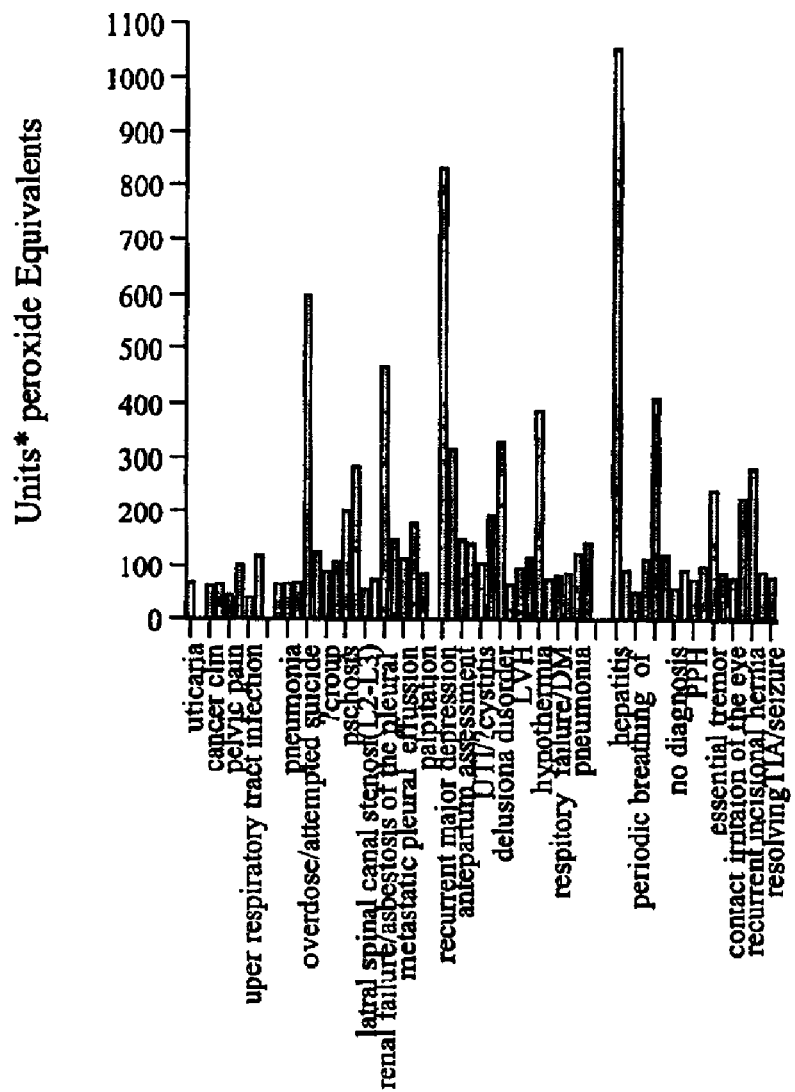

Hospital patients had urine oxidant concentrations ranging from about 0 units to 1060 units (1 unit=5 $\mu$M hydrogen peroxide equivalent), with a median of 102 units. The values for the general population ranged from 3 units to 163 units, with a median of 62 units. The hospital patients had significantly higher levels of oxidants in their urine than did the general population (2-tailed Mann-Whitney test, p=0.0022). FIG. 3a depicts individual patient oxidant levels, in comparison to oxidant levels from individual samples from the general population. FIG. 3b depicts oxidant levels in patients, with reference to illness or condition.

It is apparent from FIGS. 3a and 3b that subjects having a urine peroxide equivalent level in excess of 180 units will frequently be in need of medical attention. Furthermore, it is apparent that the assay of the present invention is useful in identifying individuals warranting medical examination. In particular, subjects having urine peroxide equivalents in excess of 100 units warrant medical examination as there is a substantial likelihood of illness or injury. Subjects having urine peroxide equivalents in excess of 200 units warrant extensive medical examination, as there is a strong possibility of illness or injury.

Thus, the assay of the present invention is useful in identifying subjects having an underlying medical condition, and in identifying subjects warranting further medical examination.

EXAMPLE 4

Solid-Support Assay for Overall Oxidative Stress

Dry polyacrylamide gel (BIOGEL, trade-mark) was reconstituted in a ferrous reaction reagent comprising 100 mM 2-deoxyglucose, 50 mM TBA, 1.4 mM EDTA and 1 mM ferrous sulfate in potassium phosphate buffer (pH7.4). One tablespoon of BIOGEL™ was placed in 100 ml of the ferrous reaction reagent and allowed to soak at 4° C. overnight. The reconstituted BIOGEL™ (polyacrylamide) gel was added to a disposable polypropylene column. 0.5 ml of urine was added to the column and allowed to diffuse, the column was incubated at 37° C. for 10 minutes and the colour change in the column was compared to the visually apparent colour change in columns to which solutions containing known amounts of hydrogen peroxide were added. The colour in the column was stable for more than one month.

The results indicate that it is possible to measure overall oxidative stress in biological fluids using an immobilized reaction reagent according to the method of the present invention.

Figure 4:
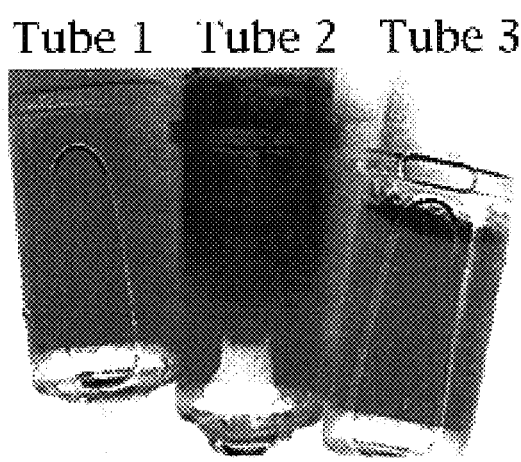
FIG. 4 is a photograph of the results of Example 4.

FIG. 4 depicts the results for 3 urine samples analyzed according to the method of Example 4. Tubes 1 and 3 depict the colour reaction of urine from the general population, whereas tube 2 depicts the visibly greater colour reaction of a patient experiencing extreme oxidative stress and suffering from severe pancreatitis. Thus, this method permits the ready identification of subjects experiencing significant oxidative stress and subjects warranting medical examination based on visual analysis of the colour reaction. The solid support method is suitable for identifying subjects having peroxide-equivalent oxidant levels in the biological fluid assayed of at least 100 units. Thus, this method is useful in identifying subjects warranting further medical attention.

The method of the present invention allows the accurate detection of overall oxidative stress using biological fluids in cases where the oxidant levels in the biological fluid are as low as 5 units. Additionally, it is possible to detect and roughly quantify oxidant levels in biological fluids visually using ferrous reaction reagent absorbed or otherwise maintained on a solid matrix such as a polyacrylamide gel column, indicating that a "dipstick" approach is feasible, as is a home test kit.

The ferrous reaction reagent of the present invention is relatively stable, and may be manufactured and sold in appropriate packaging for use in remote laboratories and veterinary clinics. Additionally, the ferrous reaction reagent may be immobilized on a suitable solid support, packaged in a substantially oxidant-free package, and sold for home use.

Thus, it is apparent that there has been provided a rapid assay for the measurement of overall oxidative stress.

While the invention has been described in conjunction with illustrated embodiments thereof, it is evident that many alternatives, modifications and variations will be apparent to those skilled in the art in light of the foregoing description. Accordingly, it is intended to embrace all such alternatives, modifications and variations as fall within the spirit and broad scope of the invention.

The embodiments of the invention in which an exclusive property or privilege is claimed are defined as follows:

1. A method of detecting hydrogen peroxides and organic peroxides in a mammalian subject said method comprising:
    a. obtaining a sample of a biological fluid from the subject;
    b. mixing the biological fluid with a ferrous reaction reagent comprising 2-deoxyglucose and a ferrous ($Fe^{2+}$) compound;
    c. incubating the biological fluid and the reaction reagent; and
    d. detecting a coloured reaction product.

2. The method of claim 1 wherein the reaction reagent comprises a solution of 2-deoxyglucose, TBA, EDTA and ferrous sulfate.

3. The method of claim 2 wherein the reaction reagent is substantially free of ascorbic acid.

4. The method of claim 2 wherein the reaction reagent comprises 2-deoxyglucose in a concentration of between about 30 and 400 mM.

5. The method of claim 2 wherein the reaction reagent comprises 2-deoxyglucose in a concentration of between about 75 and 150 mM.

6. The method of claim 2 wherein the reaction reagent comprises TBA in a concentration of between about 10 and 200 mM.

7. The method of claim 2 wherein the reaction reagent comprises EDTA in a concentration of between about 0.5 and 3 mM.

8. The method of claim 2 wherein the reaction reagent comprises ferrous sulphate in concentration of between about 0.5 and 2.0 mM.

9. The method of claim 2 wherein the reaction reagent comprises an excess of $Fe^{2+}$.

10. The method of claim 2 wherein the reaction reagent comprises 100 mM 2-deoxyglucose, 50 mM TBA, 1.4 mM EDTA, and 1 mM ferrous sulphate.

11. The method of claim 1 wherein the biological fluid is selected from the group consisting of: urine, plasma, bioreactor material and respiratory aspirate.

12. The method of claim 1 wherein one part biological fluid is mixed with between about 5 and 15 parts of the reaction reagent.

13. The method of claim 1 wherein the mixture of the biological fluid and the reaction reagent is incubated at between 20 and 45 degrees Centigrade.

14. The method of claim 1 wherein the mixtures is incubated for between about 5 and 30 minutes.

15. The method of claim 1 wherein the ferrous reaction reagent is absorbed to a solid support.

16. A method of identifying a mammalian subject in need of medical treatment comprising:
    a. obtaining a sample of biological fluid from the subject;
    b. determining oxidant level in the biological fluid by mixing the fluid with a reagent comprising 2-deoxyglucose, and a ferrous ($Fe^{2+}$) compound;
    c. incubating the fluid and the reagent and determining the presence of oxidative stress within the subject by detecting a colorimetric change in the reaction product by comparing the reaction product with a reference standard and correlating the presence of oxidative stress with a difference between the colorimetric properties of the product and the standard, thereby determining the need from medical treatment within the subject.

17. The method of claim 16 wherein the determination of oxidant level in the biological fluid comprises detecting hydrogen peroxides and organic peroxides.

18. The method of claim 16 wherein the biological fluid is selected from the group consisting of: urine, plasma, bioreactor fluid and respiratory aspirant.

19. The method of claim 16 wherein the subject is a human.

20. A ferrous reaction reagent suitable for use in assaying oxidative stress, said reaction reagent comprising 2-deoxyglucose, TBA, EDTA, and ferrous sulfate, and being substantially free of ascorbic acid.

21. The reaction reagent of claim 20 comprising 2-deoxyglucose in a concentration of between about 30 and 400 mM.

22. The reaction reagent of claim 20 comprising TBA in a concentration of between about 10 and 200 mM.

23. The reaction reagent of claim 20 comprising EDTA in a concentration of between about 0.5 and 3 mM.

24. The reaction reagent of claim 20 comprising ferrous sulphate in a concentration of between about 0.5 and 2.0 mM.

25. The reaction reagent of claim 20 comprising an excess of $Fe^{2+}$.

26. The reaction reagent of claim 20 comprising 100 mM 2-deoxyglucose, 50 mM TBA, 1.4 mM EDTA, and 1 mM ferrous sulphate.

27. The reaction reagent of claim 20 absorbed on a solid support.

28. A kit suitable for use in assaying oxidative stress from a biological fluid, said kit comprising:
    a. a ferrous reaction reagent comprising 2-deoxyglucose and a ferrous ($Fe^{2+}$) compound; and
    b. a reference standard indicating oxidant levels.

29. The kit of claim 28 further comprising instructions for detecting hydrogen peroxides and organic peroxides wherein the detecting comprises the steps of:
    (a) obtaining a sample of a biological fluid from a subject
    (b) mixing the biological fluid with the ferrous reaction reagent comprising 2-deoxyglucose and a ferrous ($Fe^{2+}$) compound;

(c) incubating the biological fluid with the reaction reagent; and (d) detecting a coloured reaction product.

30. The kit of claim 28 wherein the reaction reagent comprises 2-deoxyglucose, TBA, EDTA, and ferrous sulfate.

31. The kit of claim 30 wherein the reaction reagent is substantially free of ascorbic acid.

32. The kit of claim 28 wherein the reaction reagent is absorbed to a solid support.

33. The kit of claim 28 wherein the ferrous reaction reagent comprises 100 mM 2-deoxyglucose, 50 mM TBA, 1.4 mM EDTA, and 1 mM ferrous sulphate.

34. The kit of claim 28 wherein the standard indicating oxidant levels is based on differences in color that correspond to different oxidant levels.

35. The method of claim 1 comprising the further step of determining the presence of oxidative stress within the subject, wherein the further step comprises detecting a colorimetric change in the reaction product by comparing the reaction product with a reference standard and correlating the presence of oxidative stress with a difference between the colorimetric properties of the reaction product and the standard.

* * * * *